(12) United States Patent
Wang et al.

(10) Patent No.: US 12,216,108 B2
(45) Date of Patent: Feb. 4, 2025

(54) EVALUATION METHOD FOR ECOLOGICAL PERFORMANCE OF ASPHALT-RELATED MATERIAL

(71) Applicant: Beijing University Of Technology, Beijing (CN)

(72) Inventors: Chao Wang, Beijing (CN); Zexia Zhang, Beijing (CN); Guanyu Gong, Qian'an (CN); Yuye Wei, Qufu (CN)

(73) Assignee: Beijing University Of Technology, Beijing (CN)

( * ) Notice: Subject to any disclaimer, the term of this patent is extended or adjusted under 35 U.S.C. 154(b) by 0 days.

(21) Appl. No.: 18/736,581

(22) Filed: Jun. 7, 2024

(65) Prior Publication Data

US 2024/0410874 A1    Dec. 12, 2024

(30) Foreign Application Priority Data

Jun. 7, 2023   (CN) .......................... 202310665372.5

(51) Int. Cl.
*G01N 33/42*     (2006.01)
*G01N 33/00*     (2006.01)

(52) U.S. Cl.
CPC ......... *G01N 33/42* (2013.01); *G01N 33/0004* (2013.01)

(58) Field of Classification Search
None
See application file for complete search history.

(56) References Cited

FOREIGN PATENT DOCUMENTS

| CN | 105527412 A | * | 4/2016 | ............ G01N 33/42 |
| CN | 109670718 A | * | 4/2019 | |
| CN | 114839316 A | * | 8/2022 | |
| CN | 115112439 A | * | 9/2022 | ............... G01N 1/22 |

OTHER PUBLICATIONS

CNIPA, Notification of First Office Action for CN202310665372.5, Jul. 15, 2023.
Beijing University of Technology (Applicant), Reply to Notification of First Office Action for CN202310665372.5, w/ (allowed) replacement claims, Jul. 18, 2023.
CNIPA, Notification to grant patent right for invention in CN202310665372.5, Jul. 26, 2023.

* cited by examiner

*Primary Examiner* — Daniel S Larkin
(74) *Attorney, Agent, or Firm* — Hemisphere Law, PLLC; Zhigang Ma (57) ABSTRACT

An evaluation method for ecological performance of an asphalt-related material is provided. Firstly, working condition parameters are determined for evaluating the ecological performance of the asphalt-related material; secondly, based on the working condition parameters, a simulation test is performed on emission of asphalt-related pollutants during a preparation stage of the asphalt-related material; finally, based on a result of the simulation test, a quantitative evaluation of the ecological performance of the asphalt-related material is performed under different environmental impacts. The evaluation method is a laboratory scale simulation method based on measured pollutant emissions and various environmental impact factors, ultimately achieving laboratory scale ecological performance evaluation of the asphalt-related material, which has important reference value for green material selection of asphalt pavement.

4 Claims, 5 Drawing Sheets

EVALUATION METHOD FOR ECOLOGICAL PERFORMANCE OF ASPHALT-RELATED MATERIAL

TECHNICAL FIELD

The present disclosure relates to the technical field of evaluation for green and sustainable products of infrastructure, and particularly to an evaluation method for ecological performance of an asphalt-related material.

BACKGROUND

With the rapid development of science and technology, it has brought convenience to humanity but also caused serious environmental problems. For transportation infrastructures, asphalt pavement is a preferred pavement for expressways. However, a construction process of the asphalt pavement can cause significant environmental impacts. Specifically, asphalt-related materials release a large amount of asphalt fume during high-temperature mixing, and the composition of asphalt fume is complex and contains a large amount of harmful substances, thereby seriously threatening the health of construction personnel and the ecological environment.

At present, when an environmental impact evaluation is performed on a preparation process of an asphalt-related material, specific emission factors of asphalt fume is difficult to obtain due to the fact that the asphalt fume is usually fugitive emission, so that a comprehensive evaluation on the ecological performance of the asphalt-related material cannot be performed. Therefore, at present, a method for evaluating the direct emission and indirect emission of the asphalt-related material under high-temperature environment is lacked. How to objectively perform a quantitative evaluation on the direct emission of pollutants of the asphalt-related material and simultaneously give consideration to an evaluation on the indirect emission caused by energy consumption in a preparation process of the asphalt concrete are problems to be urgently solved in the industry. The evaluation of the asphalt-related material has important reference value for the green material selection of asphalt pavement.

SUMMARY

The present disclosure provides an evaluation method for ecological performance of an asphalt-related material. The evaluation method of the present disclosure is provided to solve the problem that fugitive emissions of pollutants during a construction process of asphalt pavement cannot be quantitatively measured, and the evaluation method of the present disclosure can comprehensively evaluate the ecological performance of the asphalt-related material, thereby achieving an ecological performance evaluation of asphalt-related material at a laboratory scale.

The present disclosure provides an evaluation method for ecological performance of an asphalt-related material. The evaluation method includes:
  determining working condition parameters for evaluating the ecological performance of the asphalt-related material;
  based on the working condition parameters, performing a first simulation test on emission of asphalt-related pollutants during a preparation stage of the asphalt-related material to obtain first simulation test results; and based on the first simulation test results, performing a quantitative evaluation on the ecological performance of the asphalt-related material under different environmental impacts.

In the evaluation method for the ecological performance of the asphalt-related material provided by the present disclosure, specifically, a process of performing the first simulation test includes:
  based on the working condition parameters, generating and collecting asphalt-related pollutants in a form of gas for the first simulation test;
  measuring concentrations of the asphalt-related pollutants to calculate an emission amount of the asphalt-related pollutants by a following formula:

$$D_i = U_m \times Q \times (T/t) \times c_i \times 10^{-6};$$

where $D_i$ represents an emission amount of asphalt-related pollutant i during the preparation stage of the asphalt-related material, $U_m$ represents a usage amount of the asphalt-related material, (represents a gas sample volume, which is controlled by a gas valve of the ventilation pipe, of the asphalt-related pollutants during the preparation stage of the asphalt-related material, T represents a sum of heating time $T_1$ and holding time $T_2$ of asphalt concrete in the working condition parameters, i.e., $T=T_1+T_2$; t represents ventilation time of a sampling bag of the sampling device during the first simulation test, and $c_i$ represents a concentration of the asphalt-related pollutant i, which is measured by the measuring device.

In the evaluation method for the ecological performance of the asphalt-related material provided by the present disclosure, specifically, processes of generating and collecting asphalt-related pollutants include:
  placing the asphalt-related material in a flue gas generation device, generating the asphalt-related pollutants in a form of gas by the flue gas generation device at a preset mixing temperature and a preset holding temperature, using a ventilation pipe to convey the asphalt-related pollutants to a sampling device; where the preset mixing temperature and the preset holding temperature in the first simulation test are consistent with the actual mixing temperature and the actual holding temperature of the asphalt-related material in the working condition parameters respectively.

In the evaluation method for the ecological performance of the asphalt-related material provided by the present disclosure, after determining working condition parameters for evaluating the ecological performance of the asphalt-related material and before performing the quantitative evaluation of the ecological performance of the asphalt-related material under different environmental impacts, the evaluation method further includes: based on the working condition parameters, performing a second simulation test on energy consumption and indirect pollutant emission during the asphalt concrete mixing stage to obtain second simulation test results.

In the evaluation method for the ecological performance of the asphalt-related material provided by the present disclosure, a process of performing the second simulation test includes:
  using a mixing device to prepare the asphalt concrete, maintaining the actual mixing temperature during the asphalt concrete mixing stage in the working condition parameters consistent with the preset mixing temperature during the preparation stage, recording energy consumption of the mixing device, and calculating an emission amount of indirect pollutants during the asphalt concrete mixing stage by a following formula, as the second simulation test results:

$$D'_i = (M_m/U_m) \times E \times F_i;$$

where $D'_i$ represents an emission amount of indirect pollutant i caused by the energy consumption of the mixing device during the asphalt concrete mixing stage, $M_m$ represents mass of asphalt in the asphalt concrete, $U_m$ represents the usage amount of the asphalt-related material, E represents the energy consumption of the mixing device, and $F_i$ represents an emission coefficient of the indirect pollutant i.

In the evaluation method for the ecological performance of the asphalt-related material provided by the present disclosure, the emission coefficient is obtained based on a proportion of different electricity generation methods and a pollutant emission coefficient of each of the different electricity generation methods.

In the evaluation method for the ecological performance of the asphalt-related material provided by the present disclosure, a process of performing the quantitative evaluation includes:
performing a characteristic calculation under each of the different environmental impacts based on the first simulation test results and the second simulation test results to obtain characteristic results, and a formula for the characteristic calculation being:

$$E_j = \sum_{i_1=1}^{Z_1} D_i \times TF_{ji_1} + \sum_{i_2=1}^{Z_2} D'_i \times TF_{ji_2};$$

where $E_j$ represents a characteristic result of environmental impact j of the asphalt-related material, $Z_1$ represents a total type number of the asphalt-related pollutants, and $TF_{ji_1}$ represents a characteristic factor of the asphalt-related pollutant i for the environmental impact j; $Z_2$ represents a total type number of the indirect pollutants; and $TF_{ji_2}$ represents a characteristic factor of the indirect pollutant i for the environmental impact j.

In the evaluation method for the ecological performance of the asphalt-related material provided by the present disclosure, the evaluation method further includes: after performing the characteristic calculation under the different environmental impacts, normalizing the characteristic results by a following formula:

$$N_j = \frac{E_j}{F_j};$$

where $N_j$ represents a normalized result of the environmental impact i of the asphalt-related material, and $F_j$ represents a normalization coefficient of the environmental impact i of the asphalt-related material.

In the evaluation method for the ecological performance of the asphalt-related material provided by the present disclosure, the different environmental impacts include global warming potential, acidification potential, photochemical oxidation potential, human toxicity potential, and eutrophication potential.

In the evaluation method for the ecological performance of the asphalt-related material provided by the present disclosure, the working condition parameters include at least one of an actual mixing temperature, actual mixing time, an actual holding temperature, and actual holding time during a preparation stage of the asphalt-related material, and at least one of an actual mixing temperature, actual mixing time, an actual holding temperature, and actual holding time during an asphalt concrete mixing stage of the asphalt-related material. In addition, not all of the working condition parameters are used in the evaluation method, those proficient in the field can select some of the working condition parameters according to actual needs.

In the evaluation method for the ecological performance of the asphalt-related material provided by the present disclosure, firstly, the working condition parameters are determined for evaluating the ecological performance of the asphalt-related material; secondly, based on the working condition parameters, simulation tests are performed on emission of asphalt-related pollutants of the asphalt-related material to obtain simulation test results; finally, based on the simulation tests, a quantitative evaluation of the ecological performance of the asphalt-related material is performed under different environmental impacts. The present disclosure provides a laboratory scale simulation method based on measured pollutant emissions and various environmental impact factors, ultimately achieving laboratory scale ecological performance evaluation of the asphalt-related material, which has important reference value for green material selection of asphalt pavement.

BRIEF DESCRIPTION OF DRAWINGS

In order to provide a clearer explanation of the technical solutions in the present disclosure or related field, a brief introduction will be given below to the accompanying drawings required in embodiments or related field. Apparently, the accompanying drawings in the following description are some embodiments of the present disclosure. For those proficient in the field, other accompanying drawings can be obtained based on these drawings without creative works.

DETAILED DESCRIPTION OF EMBODIMENTS

In order to clarify the purpose, technical solution, and advantages of the present disclosure, the following will provide a clear and complete description of the technical solutions in conjunction with the accompanying drawings. Apparently, the described embodiments are a part of the embodiments of the present disclosure, not all of them.

Based on the embodiments in the present disclosure, all other embodiments obtained by those proficient in the field without creative works fall within the scope of protection of the present disclosure.

The following describes an evaluation method for ecological performance of an asphalt-related material of the present disclosure in conjunction with FIG. 1 FIG. 2A, FIG. 2B, FIG. 2C, and FIG. 2D.

Figure 1:
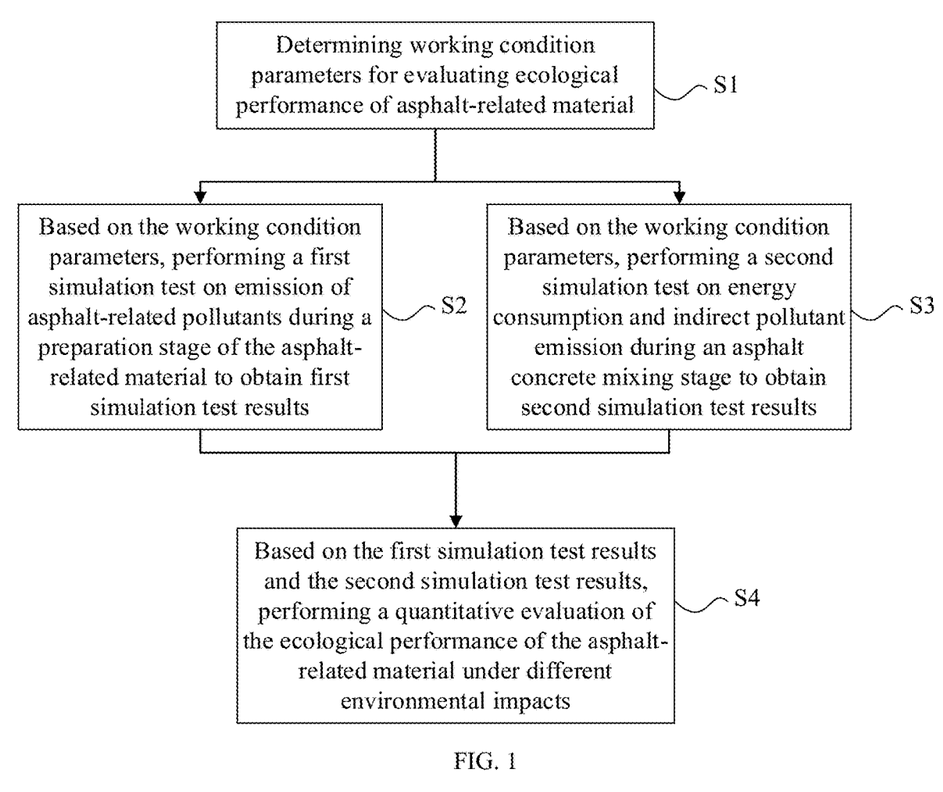
FIG. 1 illustrates a flowchart of an evaluation method for ecological performance of an asphalt-related material provided by the present disclosure.
Figure 2A:
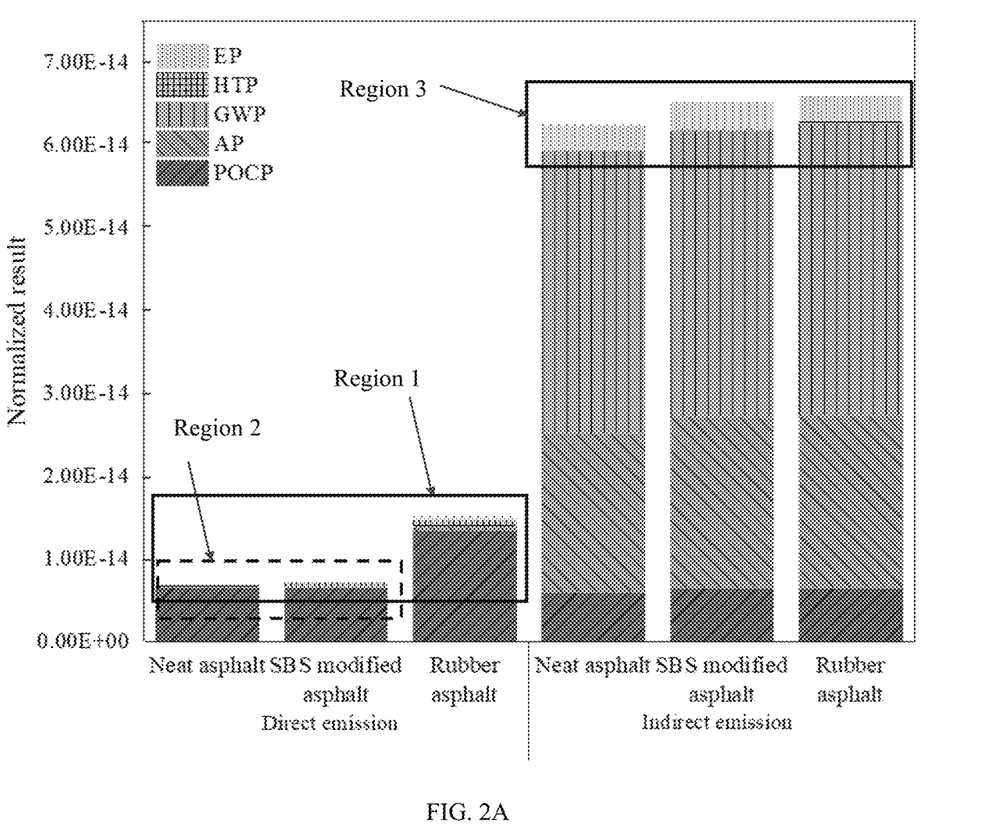
FIG. 2A illustrates a comparison diagram of normalized results of ecological performance evaluations of different asphalt-related materials in an embodiment of the present disclosure.
Figure 2B:
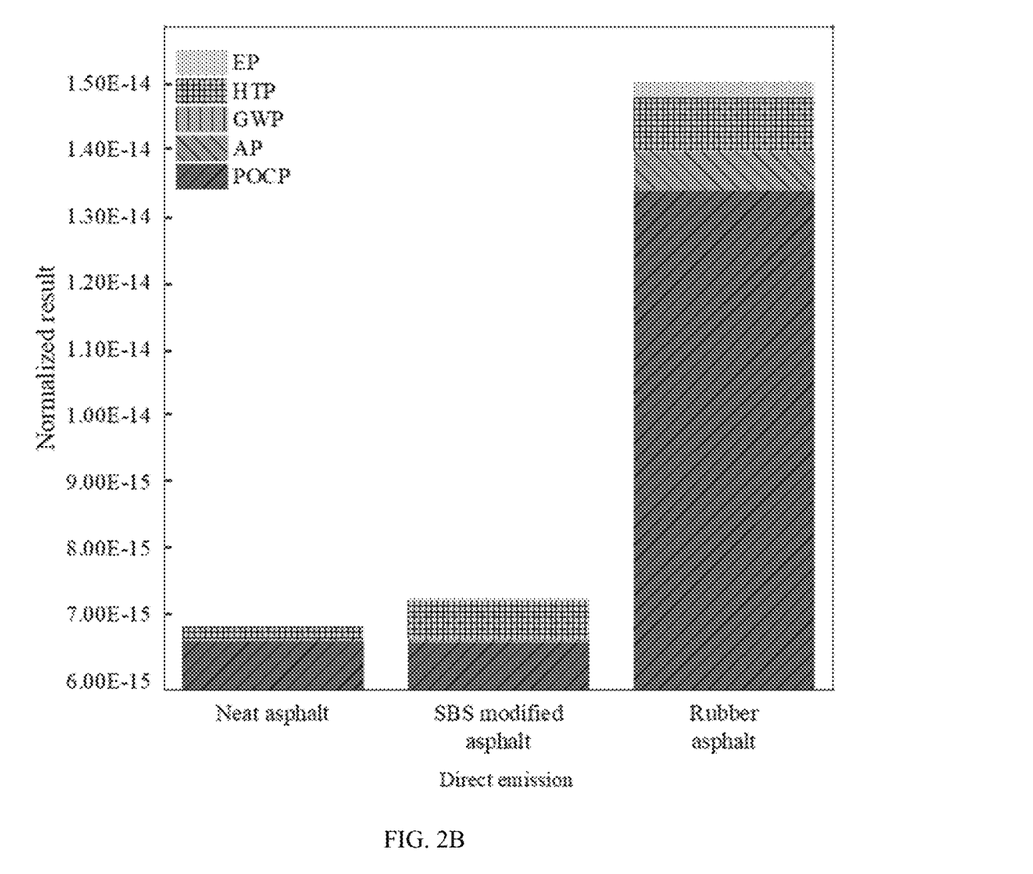
FIG. 2B illustrates an enlarged schematic view of a region 1 surrounded by a solid rectangle box in FIG. 2A.
Figure 2C:
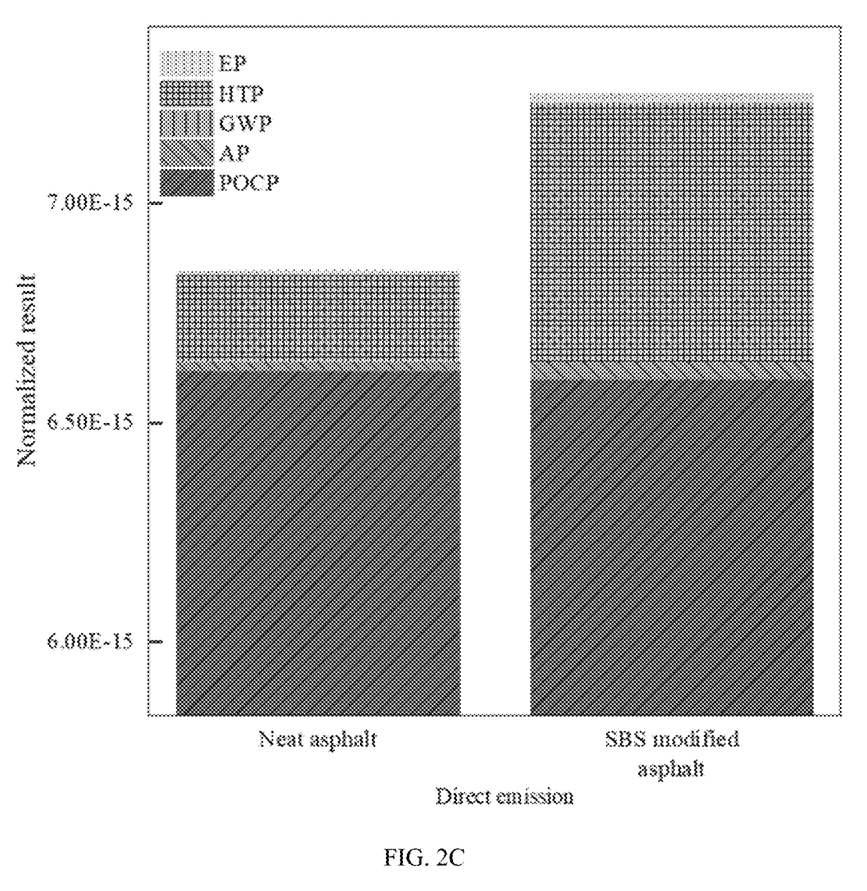
FIG. 2C illustrates an enlarged schematic view of a region 2 surrounded by a dashed rectangle box in FIG. 2A
Figure 2D:
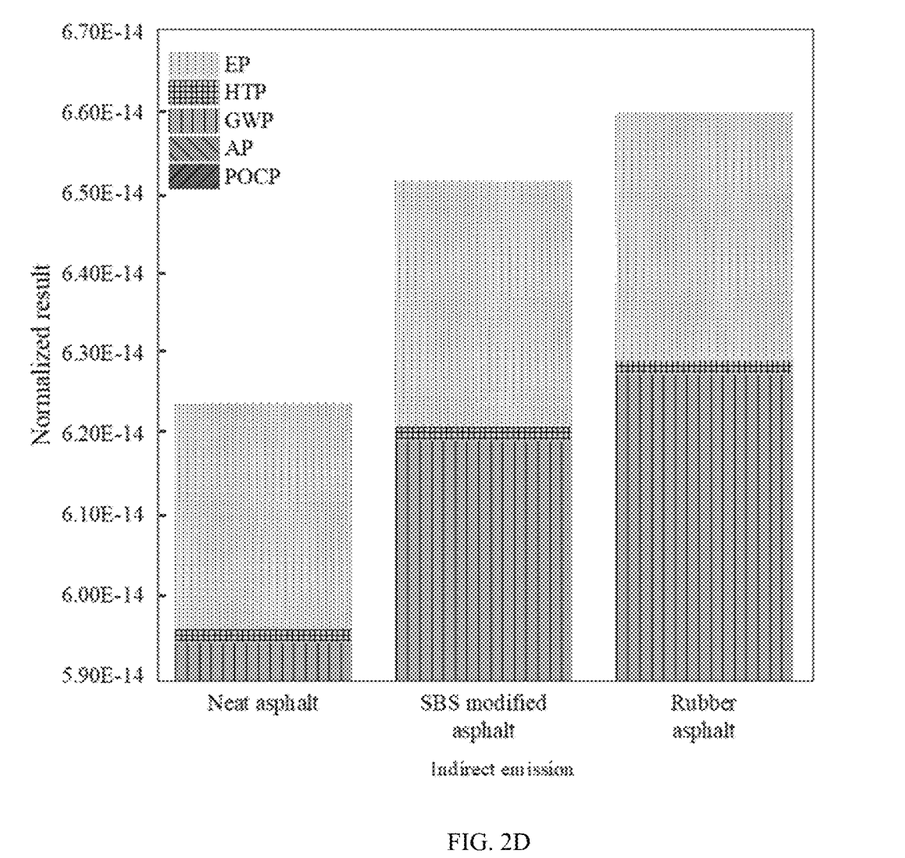
FIG. 2D illustrates an enlarged schematic view of a region 3 surrounded by a solid rectangle box in FIG. 2A.

As illustrated in FIG. 1, the evaluation method for ecological performance of an asphalt-related material provided by the present disclosure includes:

step S1: determining working condition parameters for evaluating the ecological performance of the asphalt-related material;

step S2: based on the working condition parameters, performing a first simulation test on emission of asphalt-related pollutants (also referred to as direct pollutants) during a preparation stage of the asphalt-related material to obtain simulation test results (i.e., first simulation test results); and step S4: based on simulation test results, performing a quantitative evaluation on the ecological performance of the asphalt-related material under different environmental impacts to obtain evaluation results.

In an embodiment of the present disclosure, the performing a quantitative evaluation on the ecological performance of the asphalt-related material includes performing a quantitative evaluation on direct emission of the asphalt-related pollutants (also referred to as direct pollutants) and indirect emission of indirect pollutants caused by energy consumption during an asphalt concrete mixing process.

In the step S1, the working condition parameters need to be obtained by referring to relevant technical specifications or regulations. The working condition parameters include but are not limited to the following parameters: an actual mixing temperature, actual mixing time, an actual holding temperature, and actual holding time during a preparation stage of the asphalt-related material; and an actual mixing temperature, actual mixing time, an actual holding temperature, and actual holding time during an asphalt concrete mixing stage of the asphalt-related material.

In the step S2, a process of performing the first simulation test includes:

based on the working condition parameters, generating and collecting asphalt-related pollutants in a form of gas for the first simulation test; and measuring a concentration of the asphalt-related pollutants to calculate an emission amount of the asphalt-related pollutants.

Specifically, in the first simulation test related to the emission (i.e., direct emission) of the asphalt-related pollutants during the preparation stage of the asphalt-related material, asphalt-related pollutants in a form of gas are generated by heating asphalt binders in a flue gas generation device, and the asphalt-related pollutants are collected to a sampling device by using a ventilation pipe installed with a gas valve. In an embodiment, a sampling bag can be used to collect the asphalt-related pollutants. In an embodiment of the present disclosure, the sampling device and the collection device may adopt an asphalt fume generation and collection device provided in a patent application document with the application number of CN202120787820.5. The asphalt fume generation and collection device can efficiently and conveniently collect asphalt fume components at different heating temperatures and mixing rates, which facilitates the study of the concentration and composition of the collected asphalt fume. Gas generation and collection tests (for example, a first gas collection of the asphalt-related material is completed at a mid-value of a preset mixing temperature, and then the asphalt-related material is maintained at a preset holding temperature to complete a second gas collection of the asphalt-related material) are performed at a preset mixing temperature and a preset holding temperature separately. During the gas generation and collection tests, it is necessary to ensure that temperatures of the two stages (i.e., the first gas collection and the second gas collection) are consistent with actual temperatures in engineering, in other words, the preset mixing temperature of the asphalt-related material during the preparation stage of the asphalt-related material is consistent with an actual mixing temperature of the asphalt-related material during the preparation stage of the asphalt-related material in engineering, and the preset holding temperature of the asphalt-related material is consistent with an actual holding temperature of the asphalt-related material during the preparation stage of the asphalt-related material in engineering. By simulating various parameters under actual working conditions, the present disclosure can reduce errors of test results. In some embodiments of the present disclosure, in the first simulation test of emission of asphalt-related pollutants during the preparation stage of the asphalt-related material, a heating temperature of asphalt-related material during an actual engineering mixing process can refer to relevant requirements in "Technical Specifications for Construction of Highway Asphalt Pavements" (JTG F40-2017), and the working condition parameters can be determined through this norm.

After completing the gas collections, the sampling bag directly conveys the gases (also referred to as asphalt-related pollutants or asphalt fume) to the relevant instruments, and concentrations of the gases are measured by the relevant instruments to achieve precise measurement at the laboratory level. In an embodiment of the present disclosure, the concentrations can be measured using a portable gas detector with a model number of PGM-62x8. A calculation method for different asphalt-related pollutants is shown in formula (1):

$$D_i = U_m \times Q \times (T/t) \times c_i \times 10^{-6}; \quad (1)$$

where $D_i$ represents an emission amount (the unit of the emission amount is kilograms (kg)) of asphalt-related pollutant i during the preparation stage of the asphalt-related material, $U_m$ represents a usage amount (the unit of the usage amount is kg) of the asphalt-related material, (represents a gas sample volume (the unit of the gas sample volume is liter/minute (L/min)) of the asphalt-related pollutants during the preparation stage of the asphalt-related material; $T=T_1+T_2$, and T represents a sum of heating time $T_1$ (the unit of the heating time is min) and holding time $T_2$ (the unit of the holding time is min) of asphalt concrete in the working condition parameters; t represents ventilation time (the unit of the ventilation time is min) of a sampling bag of the sampling device during the first simulation test, and $c_i$ represents a concentration (the unit of the concentration is milligram/minute (mg/min)) of the asphalt-related pollutant i measured by a measuring device.

In a preferred embodiment of the disclosure, after step S1 (determining working condition parameters for evaluating the ecological performance of asphalt-related material) and before the step S4 (performing the quantitative evaluation on the ecological performance of the asphalt-related material under different environmental impacts), the evaluation method further includes step S3: based on the working condition parameters, performing a second simulation test on energy consumption and indirect pollutant emission during the asphalt concrete mixing stage. It should be understood that there is no specific temporal relationship between steps S3 and S2, and they may be not executed at the same time or may be executed at the same time. The present disclosure does not limit the temporal relationship between steps S3 and S2.

Specifically, the second simulation test of the energy consumption and indirect pollutant emission during the asphalt concrete mixing stage is as follows.

In the second simulation test of the energy consumption and indirect pollutant emission during the asphalt concrete mixing stage, a mixing device is used to prepare the asphalt concrete. A preparation process of the asphalt concrete includes: firstly, drying and screening aggregates, preheating asphalt and mineral powder, then sequentially adding the aggregates, the asphalt, and the mineral powder to the mixing device for mixing until the asphalt concrete is formed. In the preparation process of the asphalt concrete, a preset mixing temperature during the asphalt concrete mixing stage is maintained consistent with an actual mixing temperature of the working condition parameters in engineering, thereby minimizing errors of the test result as much as possible. The energy consumption of the mixing device is recorded, and an emission amount of indirect pollutants is calculated during the asphalt concrete mixing stage by a following formula (2):

$$D'_i = (M_m/U_m) \times E \times F_i. \qquad (2)$$

In the formula (2), $D_i'$ represents an emission amount (the unit of the emission amount is kg) of indirect pollutant i during the asphalt concrete mixing stage, $M_m$ represents mass (the unit of the mass is kg) of asphalt in the asphalt concrete, $U_m$ represents the usage amount of the asphalt-related material, E represents the energy consumption (the unit of the energy consumption is kilogram of coal equivalent (kgce)) of the mixing device, and $F_i$ represents an emission coefficient (the unit of the emission coefficient is kg/kg) of the indirect pollutant i. It should be noted that a method to acquire energy consumption of the mixing device is common knowledge for those proficient in the field.

In an embodiment, in the second simulation test of the energy consumption and indirect pollutant emission during the asphalt concrete mixing stage, it is necessary to use the mixing device in the laboratory and refer to the "Standard Test Methods of Bitumen and Bituminous Mixtures for Highway Engineering" (JTG E20-2011) for the preparation process of the asphalt concrete, and the working condition parameters are determined according to the regulation.

In the step S4, based on results of the first simulation test and the second simulation test, a process of performing the quantitative evaluation includes: performing a characteristic calculation under the different environmental impacts based on the results of the first simulation test and the second simulation test. The characteristic calculation under the different environmental impacts can reflect impacts caused by pollutants (i.e., the asphalt-related pollutants and the indirect pollutants), thereby achieving a comprehensive evaluation. A formula for the characteristic calculation is:

$$E_j = \sum_{i_1=1}^{Z_1} D_i \times TF_{ji_1} + \sum_{i_2=1}^{Z_2} D'_i \times TF_{ji_2}. \qquad (3)$$

In the formula (3), $E_j$ represents a characteristic result of environmental impact j of the asphalt-related material, $Z_1$ represents a total type number of the asphalt-related pollutants, and $TF_{ji_1}$ represents a characteristic factor of the asphalt-related pollutant i for the environmental impact j; $Z_2$ represents a total type number of the indirect pollutants; and $TF_{ji_2}$ represents a characteristic factor of the indirect pollutant i for the environmental impact j. The characteristic factors can be obtained by querying the ReCiPe environmental impact assessment method, and a webpage link for this method is https://link.springer.com/content/pdf/10.1007/s11367-016-1246-y.pdf.

In an embodiment of the present disclosure, the different environmental impacts include global warming potential (GWP), acidification potential (AP), photochemical oxidation potential (POCP), human toxicity potential (HTP), and eutrophication potential (EP). In the formula (3), j=1, 2, 3, 4, and 5 respectively represent global warming potential, acidification potential, photochemical oxidation potential, human toxicity potential, and eutrophication potential. When j is not equal to 1, $I_{co2e}=0$. $I_{co2e}$ represents equivalent carbon dioxide emission during the second simulation test.

In an embodiment, after performing the characteristic calculation under the different environmental impacts, in order to further compare the relative sizes of the different environmental impacts, it is necessary to normalize the characterization result obtained from the above calculations, so that the results of each environmental impact can be converted into the same dimension. The characteristic result is normalized by a following formula (4):

$$N_j = \frac{E_j}{F_j}. \qquad (4)$$

In the formula (4), $N_j$ represents a normalized result of the environmental impact j of the asphalt-related material, and $F_j$ represents a normalization coefficient of the environmental impact j of the asphalt-related material.

In order to provide a more detailed explanation of the evaluation method for ecological performance of asphalt-related material provided by the present disclosure, a specific example will be used below for illustration.

In the specific embodiment, 70 #neat asphalt, SBS modified asphalt (SBS is a triblock copolymer with styrene and butadiene as monomers) and 20% rubber asphalt are used in an asphalt pavement engineering of a first grade highway in a northern province of China. An asphalt concrete mixing stage in the actual engineering is simulated according to laboratory scale direct and indirect emission tests (i.e., the first simulation test and the second simulation test) proposed by the present disclosure. The specific embodiment selects unit weight (1 kg) as a reference unit to quantitatively evaluate the ecological performance of asphalt-related material. It should be understood that in an evaluation process of the ecological performance of asphalt-related material, if only the direct emission of asphalt-related pollutants during a preparation stage of the asphalt-related material needs to be evaluated, the step S3 can be skipped after performing the step S2, and the step S4 can be directly performed.

In the specific embodiment, the step S1 of the evaluation method includes: determining working condition parameters for evaluating the ecological performance of asphalt-related material.

Evaluations of the ecological performance of asphalt-related material can be divided into direct emission of the asphalt-related pollutants and indirect emission of the indirect pollutants caused by energy consumption during the asphalt concrete mixing stage.

For the actual mixing temperature of the asphalt-related material in actual engineering, the actual mixing temperature can be determined according to the relevant requirements in the "Technical Specifications for Construction of Highway Asphalt Pavements" (JTG F40-2017). Mixing temperatures of the neat asphalt, the SBS modified asphalt, and the rubber asphalt are set at 155-165° C., 165-175° C., and 170-185° C., respectively. Holding temperatures are 10° C. lower than the mixing temperatures, and heating time and holding time are set at 5 minutes and 10 minutes, respectively.

In the specific embodiment, the step S2 of the evaluation method includes: performing a first simulation test on emission of asphalt-related pollutants during the preparation stage of the asphalt-related material to obtain first simulation test results.

In the first simulation test of the emission (i.e., the direct emission) of direct pollutants during the preparation stage of the asphalt-related material, a flue gas generation device is used for heating asphalt binders to generate gases (i.e., pollutants), and the gases are collected into a sampling bag by using a ventilation pipe installed with a gas valve. Gas generation and collection tests are performed at the preset mixing temperature and the preset holding temperature. The preset mixing temperature is consistent with the actual mixing temperature of the asphalt-related material in the actual engineering determined in the step S1, and the preset holding temperature is consistent with the actual holding temperature of the asphalt-related material in the engineering project determined in the step S1. In an embodiment, the preset mixing temperatures of the neat asphalt, the SBS modified asphalt, and the rubber asphalt are 160° C., 170° C., and 180° C., respectively, and the preset holding temperatures of the neat asphalt, the SBS modified asphalt, and the rubber asphalt are 150° C., 160° C., and 170° C., respectively. During the first simulation test, three types of asphalt-related materials complete a first gas collection at the preset mixing temperature, and then the three types of asphalt-related materials complete a second gas collection at the preset holding temperature. Finally, concentrations of the pollutants in the sampling bag are measured by relevant instruments. A calculation method for each type of the pollutants is shown in formula (1), and a simulation test result of direct emissions of 1 kg of each asphalt-related material are shown in TABLE 1. NMVOC in TABLE 1 represents non-methane volatile organic compounds, while NOx represents nitrogen oxides.

TABLE 1

Simulation test result of direct emission of each asphalt-related material

| Item | Unit | Neat asphalt | SBS modified asphalt | Rubber asphalt |
|---|---|---|---|---|
| $CO_2$ | kg/kg | 3.00E−07 | 3.00E−07 | 3.00E−07 |
| $SO_2$ | kg/kg | 0.00E+00 | 0.00E+00 | 1.58E−05 |
| $NO_x$ | kg/kg | 8.10E−06 | 1.67E−05 | 2.29E−04 |

TABLE 1-continued

Simulation test result of direct emission of each asphalt-related material

| Item | Unit | Neat asphalt | SBS modified asphalt | Rubber asphalt |
|---|---|---|---|---|
| NMVOC | kg/kg | 7.23E−04 | 7.21E−04 | 1.45E−03 |
| $H_2S$ | kg/kg | 5.17E−06 | 1.46E−05 | 1.43E−04 |
| Particulate matter | kg/kg | 1.20E−02 | 3.60E−02 | 4.90E−02 |

In the specific embodiment, the step S3 of the evaluation method includes: performing a second simulation test on energy consumption and indirect pollutant emission during the asphalt concrete mixing stage to obtain second simulation test results.

For the second simulation test of the energy consumption and indirect pollutant emission during the asphalt concrete mixing stage, a mixing device in a laboratory is used for the second simulation test, and the preparation of the asphalt concrete is performed by referring to the "Standard Test Methods of Bitumen and Bituminous Mixtures for Highway Engineering" (JTG E20-2011). In an embodiment, in the second simulation test of the energy consumption and indirect pollutant emission during the asphalt concrete mixing stage, preset mixing temperatures of aggregates of the neat asphalt, the SBS modified asphalt, and the rubber asphalt are consistent with the mixing temperatures of the neat asphalt, the SBS modified asphalt, and the rubber asphalt in the first simulation test of emission of asphalt-related pollutants during the preparation stage of the asphalt-related material, respectively. For example, the preset mixing temperatures for aggregates of the neat asphalt, the SBS modified asphalt, and the rubber asphalt are 160° C., 170° C., and 180° C., respectively. During the second simulation test, mass of the asphalt concrete, an asphalt content, and energy consumption of the mixing device are recorded. In the specific embodiment, the mixing device only relies on electricity for energy supply, and a pollutant emission coefficient caused by electricity consumption is obtained based on a proportion of different electricity generation methods published by the national bureau of statistics of China and pollutant emission coefficients of the different electricity generation methods. In the specific embodiment, the pollutant emission of $CO_2$, $SO_2$, $NO_X$, and particulate matters from 1 kWh of electricity are 5.88E−01 kg, 2.44E−04 kg, 2.33E−04 kg, and 5.73E−05 kg, respectively. The calculation method for indirect emission during a preparation stage of the asphalt concrete is shown in the above formula (2), and a simulation test result during the asphalt concrete mixing stage are shown in TABLE 2.

TABLE 2

Simulation test result of indirect emission during the asphalt concrete mixing stage

| Item | Unit | Neat asphalt | SBS modified asphalt | Rubber asphalt |
|---|---|---|---|---|
| $CO_2$ | kg/kg | 6.23E+00 | 7.05E+00 | 7.64E+00 |
| $SO_2$ | kg/kg | 2.59E−03 | 2.93E−03 | 3.17E−03 |
| $NO_x$ | kg/kg | 2.47E−03 | 2.80E−03 | 3.03E−03 |
| Particulate matter | kg/kg | 6.07E−04 | 6.87E−04 | 7.45E−04 |

In the specific embodiment, the step S4 of the evaluation method includes: based on the first simulation test results and the second simulation test results, performing a quantitative evaluation of the ecological performance of the asphalt-related material under different environmental impacts to obtain characteristic results.

Based on the simulation test results of direct emission and indirect emissions of the asphalt-related materials, GWP, AP, POCP, HTP, and EP are selected as the different environmental impacts for the quantitative evaluation of the ecological performance, and the influencing factors and main pollutants of the different environmental impacts are classified as shown in TABLE 3.

TABLE 3

Types of environmental impacts and the main pollutants

| Types of environmental impacts | Unit | Main pollutants |
|---|---|---|
| GWP | kg-$CO_2$.eq · $yr^{-1}$ | $CO_2$, etc |
| AP | kg-$SO_2$.eq · $yr^{-1}$ | $SO_2$, $NO_X$, etc |
| POCP | kg-ethylene.eq·$yr^{-1}$ | $SO_2$, $NO_X$, NMVOC, etc |
| HTP | kg-1,4-dichlorobenzene.eq · $yr^{-1}$ | $SO_2$, $NO_X$, particulate matters, etc |
| EP | kg-$PO_4^{3-}$.eq · $yr^{-1}$ | $NO_X$, COD, $PO_4^{3-}$, etc |

The emission data list of the pollutants is characterized based on selected characteristic factors. Through this step, the pollutants that cause the same environmental impact can be merged. Data of the emission data list can be converted into the same unit using the characteristic factors, and the merged result of the characteristic factors of the ecological performance of the asphalt-related materials is shown in TABLE 4.

TABLE 4

Characteristic results of the ecological performance of the asphalt-related materials

| | Emission of asphalt-related pollutants | | | Emission of indirect pollutants caused by energy consumption | | |
|---|---|---|---|---|---|---|
| Item | Neat asphalt | SBS modified asphalt | Rubber asphalt | Neat asphalt | SBS modified asphalt | Rubber asphalt |
| GWP | 3.00E−07 | 3.00E−07 | 3.00E−07 | 1.33E+00 | 1.34E+00 | 1.37E+00 |
| AP | 5.67E−06 | 1.17E−05 | 1.76E−04 | 5.71E−03 | 6.19E−03 | 6.22E−03 |
| POCP | 3.01E−04 | 3.00E−04 | 6.09E−04 | 2.74E−04 | 2.97E−04 | 2.99E−04 |
| HTP | 9.86E−03 | 2.95E−02 | 4.05E−02 | 8.07E−03 | 8.78E−03 | 8.82E−03 |
| EP | 1.05E−06 | 2.17E−06 | 2.98E−05 | 3.63E−04 | 3.94E−04 | 3.96E−04 |

The characterization process obtains load values for each type of the environmental impacts, but the characteristic results only represent the absolute values of the total amount. In order to further compare relative sizes of the different environmental impacts, it is necessary to use the characteristic factors to normalize the characteristic results, thereby obtaining a single environmental impact indicator value to illustrate comparison data of the different environmental impacts. Normalized results of the asphalt-related materials are shown in TABLE 5.

TABLE 5

Normalized results of the asphalt-related materials

| | Emission of asphalt-related pollutants | | | Emission of indirect pollutants caused by energy consumption | | |
|---|---|---|---|---|---|---|
| Item | Neat asphalt | SBS modified asphalt | Rubber asphalt | Neat asphalt | SBS modified asphalt | Rubber asphalt |
| GWP | 7.77E−21 | 7.77E−21 | 7.77E−21 | 3.43E−14 | 3.47E−14 | 3.54E−14 |
| AP | 1.90E−17 | 3.91E−17 | 5.89E−16 | 1.91E−14 | 2.07E−14 | 2.08E−14 |
| POCP | 6.62E−15 | 6.60E−15 | 1.34E−14 | 6.02E−15 | 6.53E−15 | 6.56E−15 |
| HTP | 1.98E−16 | 5.93E−16 | 8.13E−16 | 1.62E−16 | 1.76E−16 | 1.77E−16 |
| EP | 8.16E−18 | 1.68E−17 | 2.31E−16 | 2.81E−15 | 3.05E−15 | 3.07E−15 |

Based on the normalized results of the environmental impacts, the differences of the ecological performance among the different asphalt-related materials can be compared.

As shown in FIG. 2A through FIG. 2D, when a normalized result is greater, the environmental load caused by a corresponding asphalt-related material is greater, which indicates the ecological performance of the corresponding asphalt-related material is worse. As shown in FIG. 2A through FIG. 2D, it can be seen that the environmental impacts caused by the direct emission (i.e., three bars on the left of FIG. 2A) during the preparation stage of asphalt-related materials are mainly POCP and HTP. Furthermore, the ecological performance of the rubber asphalt is much lower than that of the neat asphalt and the SBS modified asphalt. Environmental impacts caused by the indirect emission (i.e., three bars on the right of FIG. 2A) during the asphalt concrete mixing stage are mainly GWP and AP. GWP and AP caused by the SBS modified asphalt and the rubber asphalt are slightly worse than that of the neat asphalt.

In an embodiment, the evaluation method for the ecological performance of the asphalt-related material further includes: determining, based on the characteristic results of the asphalt-related material, whether the asphalt-related material satisfies a pavement requirement; and in response to the asphalt-related material satisfying a pavement requirement, applying the asphalt-related material to asphalt pavement.

In an embodiment, the determining, based on the characteristic results of the asphalt-related material, whether the asphalt-related material satisfies a pavement requirement includes: in response to the characteristic results being smaller than respective preset characteristic values, determining that the asphalt-related material satisfies a pavement requirement. Specifically, the preset characteristic values are set according to actual needs, which are not limited herein.

To sum up, the evaluation method for the ecological performance of the asphalt-related material provided by the present disclosure provides a laboratory-scale simulation means aiming at the problem that fugitive emission of pollutants cannot be accurately, effectively and quantitatively measured and calculated in a construction process of asphalt pavement, and the evaluation method of the present disclosure solves the problem of quantitative evaluation of the ecological performance of high-temperature emission in the preparation stage of the asphalt-related material. The evaluation method is based on the simulation tests of the direct emission of pollutants and the indirect emissions of pollutants generated by energy consumption in the asphalt concrete mixing stage. In a process of quantifying the environmental impacts, a life cycle assessment technology framework is used as a theoretical basis. By measuring the emission of pollutants and based on environmental impact factors of pollutants, the evaluation of ecological performance of asphalt-related material at the laboratory scale is finally achieved, the evaluation method of the present disclosure has important reference value for green material selection of asphalt pavement.

Finally, it should be noted that the above embodiments are only used to illustrate the technical solutions of the present disclosure, while not to limit the present disclosure. Although the present disclosure has been described in detail with reference to the above embodiments, those proficient in the field should understand that they can still modify the technical solutions recorded in the above embodiments or equivalently replace some of the technical features thereof, and these modifications or replacements do not separate the essence of corresponding technical solutions from the spirit and scope of the technical solutions of the embodiments of the present disclosure.

What is claimed is:

1. An evaluation method for ecological performance of an asphalt-related material, comprising:
   determining working condition parameters for evaluating the ecological performance of the asphalt-related material; wherein the working condition parameters comprise at least one of an actual mixing temperature, actual mixing time, an actual holding temperature, and actual holding time during a preparation stage of the asphalt-related material, and at least one of an actual mixing temperature, actual mixing time, an actual holding temperature, and actual holding time during an asphalt concrete mixing stage of the asphalt-related material;
   based on the working condition parameters, performing a first simulation test on emission of asphalt-related pollutants during the preparation stage of the asphalt-related material to obtain first simulation test results; wherein a process of performing the first simulation test comprises performing a gas generation and collection test on the asphalt-related material based on the working condition parameters, comprising: placing the asphalt-related material in a flue gas generation device to generate the asphalt-related pollutants in a form of gas at a preset mixing temperature and a preset holding temperature, using a ventilation pipe to convey the asphalt-related pollutants to a sampling device, measuring concentrations of the asphalt-related pollutants by a measuring device, and calculating an emission amount of the asphalt-related pollutants during the preparation stage of the asphalt-related material by a following formula, as the first simulation test results:

$$D_i = U_m \times Q \times (T/t) \times c_i \times 10^{-6};$$

where $D_i$ represents an emission amount of asphalt-related pollutant i during the preparation stage of the asphalt-related material, $U_m$ represents a usage amount of the asphalt-related material, Q represents a gas sample volume, which is controlled by a gas valve of the ventilation pipe, of the asphalt-related pollutants during the preparation stage of the asphalt-related material, T represents heating time or holding time of asphalt concrete in the working condition parameters, t represents ventilation time of a sampling bag of the sampling device during the first simulation test, and $c_i$ represents a concentration of the asphalt-related pollutant i, which is measured by the measuring device;

based on the working condition parameters, performing a second simulation test on energy consumption and indirect pollutant emission during the asphalt concrete mixing stage to obtain second simulation test results; wherein a process of performing the second simulation test comprises: using a mixing device to prepare the asphalt concrete, maintaining the actual mixing temperature during the asphalt concrete mixing stage in the working condition parameters consistent with the preset mixing temperature during the preparation stage, recording energy consumption of the mixing device, and calculating an emission amount of indirect pollutants during the asphalt concrete mixing stage by a following formula, as the second simulation test results:

$$D'_i = (M_m/U_m) \times E \times F_i;$$

where $D'_i$ represents an emission amount of indirect pollutant i caused by the energy consumption of the mixing device during the asphalt concrete mixing stage, $M_m$ represents mass of asphalt in the asphalt concrete, $U_m$ represents the usage amount of the asphalt-related material, E represents the energy consumption of the mixing device, and $F_i$ represents an emission coefficient of the indirect pollutant i;

based on the first simulation test results and the second simulation test results, performing a quantitative evaluation on the ecological performance of the asphalt-related material under different environmental impacts; wherein a process of performing the quantitative evaluation comprises: performing a characteristic calculation under each of the different environmental impacts based on the first simulation test results and the second simulation test results to obtain characteristic results, and a formula for the characteristic calculation being:

$$E_j = \sum_{i=1}^{z}(D_i + D'_i) \times TF_{ji};$$

where $E_j$ represents a characteristic result of environmental impact j of the asphalt-related material, z represents a total type number of the asphalt-related pollutants, and $TF_{ji}$ represents a characteristic factor of the asphalt-related pollutant i for the environmental impact j; and the different environmental impacts comprise global warming potential, acidification potential, photochemical oxidation potential, human toxicity potential, and eutrophication potential.

2. The evaluation method for the ecological performance of the asphalt-related material as claimed in claim 1, wherein the preset mixing temperature and the preset holding temperature in the first simulation test are consistent with the actual mixing temperature and the actual holding temperature during a preparation stage of the asphalt-related material in the working condition parameters respectively.

3. The evaluation method for the ecological performance of the asphalt-related material as claimed in claim 1, wherein the emission coefficient is obtained based on a proportion of different electricity generation methods and a pollutant emission coefficient of each of the different electricity generation methods.

4. The evaluation method for the ecological performance of the asphalt-related material as claimed in claim 1, further comprising: after performing the characteristic calculation under the different environmental impacts, normalizing the characteristic results by a following formula:

$$N_j = \frac{E_j}{F_j};$$

where $N_j$ represents a normalized result of the environmental impact j of the asphalt-related material, and $F_j$ represents a normalization coefficient of the environmental impact j of the asphalt-related material.

* * * * *